(12) United States Patent
Choikhet

(10) Patent No.: US 9,417,219 B2
(45) Date of Patent: Aug. 16, 2016

(54) SAMPLE SEPARATION DEVICE WITH VALVE

(75) Inventor: Konstantin Choikhet, Boeblingen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1233 days.

(21) Appl. No.: 12/619,283

(22) Filed: Nov. 16, 2009

(65) Prior Publication Data

US 2011/0116973 A1    May 19, 2011

(51) Int. Cl.
 *G01N 30/02*   (2006.01)
 *G01N 30/38*   (2006.01)
 *G01N 30/34*   (2006.01)
 *G01N 30/20*   (2006.01)

(52) U.S. Cl.
 CPC ............... *G01N 30/38* (2013.01); *G01N 30/34* (2013.01); *G01N 30/20* (2013.01); *G01N 2030/347* (2013.01)

(58) Field of Classification Search
 CPC ............................ G01N 30/02; G01N 30/38
 USPC ........... 422/70, 89; 436/161; 73/23.35, 23.36, 73/23.42, 61.52, 61.56; 95/82–89; 96/101–107; 210/198.2, 656
 See application file for complete search history.

(56) References Cited

U.S. PATENT DOCUMENTS

| | | | |
|---|---|---|---|
| 2007/0000313 A1* | 1/2007 | Weissgerber | 73/61.56 |
| 2007/0181505 A1* | 8/2007 | DeMarco | 210/656 |
| 2008/0093300 A1* | 4/2008 | Clarke et al. | 210/656 |

* cited by examiner

*Primary Examiner* — Jan Ludlow

(57) ABSTRACT

A sample separation device for separating a sample comprises a first fluid supply path for supplying a first fluid, a second fluid supply path for supplying a second fluid, a sample separation unit adapted for separating the sample, a sensor configured for determining a value of a parameter related to the fluid, and a valve configured for selectively coupling both of the first and second fluid supply paths to the sensor and to the sample separation unit, or coupling one of the first and second fluid supply paths to the sensor.

12 Claims, 4 Drawing Sheets

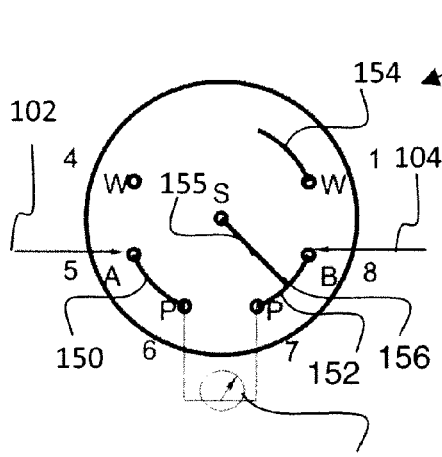
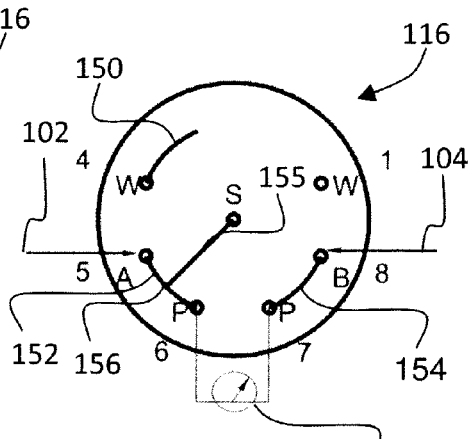
Fig. 2A    Fig. 2B
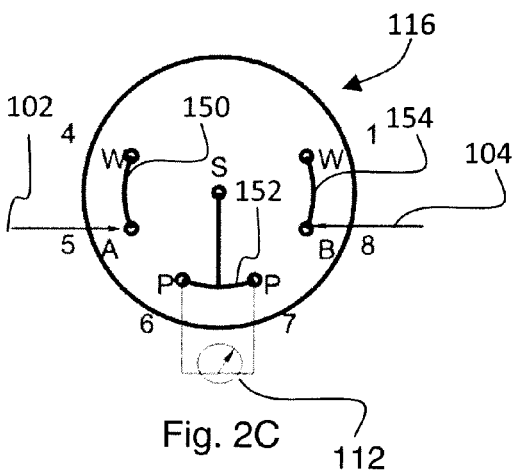
Fig. 2C
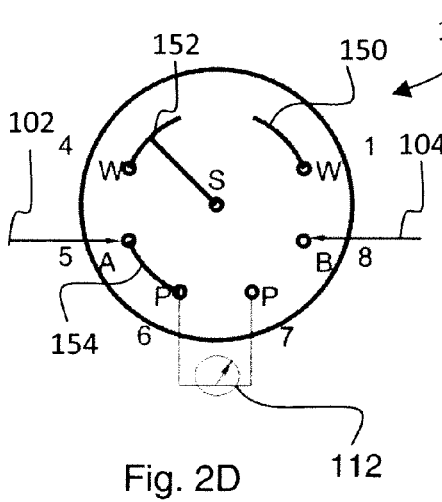
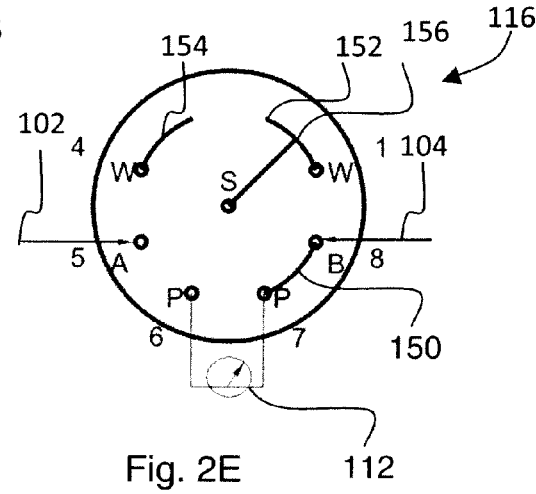
Fig. 2D    Fig. 2E

SAMPLE SEPARATION DEVICE WITH VALVE

BACKGROUND

The present invention relates to a sample separation device, in particular for high performance liquid chromatography application.

In high performance liquid chromatography (HPLC), a liquid has to be provided usually at a very well controlled flow rate (e.g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid containing compounds to be separated is driven through a stationary phase (e.g. contained in a chromatographic column), thus separating different compounds of the sample which may then be identified.

The mobile phase, for example, a solvent, is pumped under high pressure typically through a column filled with packing material, and the sample (e.g. a chemical or biological mixture) to be analyzed is injected into the column. As the sample passes through the column driven by the liquid flow, the different compounds, each one having a different affinity for the packing medium, move through the column with different velocities. Those compounds having higher affinity to the stationary phase (e.g. a packing medium) move more slowly through the column than those having lower affinity, and this velocity differences results in the compounds being separated from one another as they pass through the column.

During operation, a flow of the mobile phase, typically driven by a high pressure chromatographic pump, traverses the column filled with the stationary phase, and due to the interactions between the mobile, the stationary phase and sample components a separation of different compounds may be achieved. As a result of flow passing through the stationary phase and depending on the physical properties of the stationary phase and the mobile phase, a relatively high pressure drop takes place along the column. The composition of the mobile phase is in many cases controlled by the pump operation, as the pump provides single flows of mobile phase constituents according to the pump settings or program. These flows are then combined together to provide a mixed flow of the mobile phase or eluent. The composition and the flow rate of the mobile phase are usually precisely controlled.

In case of a leak in a fluidic supply path such as in a conduit upstream of a sample separation device, the flow and sometimes also the composition of the delivered mobile phase will be altered or disturbed, which may deteriorate proper operation of the separation system. Already minor leakages may affect the reproducibility and accuracy of the operation of the separation system. Major leaks that can lead to loss of detectable amount of liquid lead to operation stop.

JP 2005257609 discloses a liquid chromatography device intending to detect a liquid leakage in the whole system of the liquid chromatography device without using a flow sensor.

WO2009/062538, by the same applicant Agilent Technologies, discloses that in a high performance liquid chromatography system, wherein a mobile phase is driven through a stationary phase for separating compounds of a sample fluid comprised in the mobile phase, a flow rate of the mobile phase is controlled in dependence on a variation in a control value in the system.

SUMMARY

It is an object of the invention to provide an improved sample separation in particular for HPLC applications. The object is solved by the independent claim(s). Further embodiments are shown by the dependent claim(s).

According to the present invention, a sample separation device for separating a sample comprises a first fluid supply path for supplying a first fluid, a second fluid supply path for supplying a second fluid, a sample separation unit adapted for separating the sample, a sensor configured for determining a value of a parameter related to the fluid, and a valve. The valve is configured for selectively coupling both of the first and second fluid supply paths to the sensor and to the sample separation unit, or coupling one of the first and second fluid supply paths to the sensor.

The configuration of the valve allows using one sensor for sensing—during "regular operation" (i.e. when at least one of the first and second fluid supply paths supplying fluid to the sample separation unit)—a flow property representative for the output flow into the system (i.e. towards the sample separation unit), as well as for diagnosing each one of the first and second fluid supply paths separately.

In an embodiment, the valve is further configured for mixing the first and second fluid while coupling both of the first and second fluid supply paths to the sensor and to the sample separation unit. This can be accomplished internally or externally in respect to the valve. In the first case, the mixing point (i.e. where the first and second fluids commonly enter a same conduit) is located within the valve and might be a part of the valve. In the latter case, the mixing point is located outside of the valve but coupled thereto.

The valve can further be configured for coupling at least one of the first and second fluid supply paths to a waste outlet, thus allowing purging each one or both of the first and second fluid supply paths.

The valve can also be configured for coupling the sample separation unit to a waste outlet while coupling the one of the first and second fluid supply paths to the sensor.

In an embodiment, the valve is configured for blocking one of the first and second fluid supply paths, while the sensor is coupled to the blocked fluid supply paths before the blockage. Thus, each supply path can be sensed individually by the sensor.

In an embodiment, the valve is configured for coupling the sample separation unit to a waste outlet, while coupling one of the first and second fluid supply paths to the sensor, and blocking it.

The parameter determined by the sensor can be related to a state of the fluid. Preferably, the parameter is one of pressure and flow rate of the fluid.

According to an exemplary embodiment of the present invention, the sample separation device (such as a liquid chromatography device) for separating the sample (such as a fluidic sample) comprises a mixing point (such as a junction of the first fluid supply path and the second fluid supply path) in fluid communication with and arranged downstream (for instance in relation to a fluid flow direction) of the first fluid supply path and the second fluid supply path and adapted for mixing the first fluid (which may originate from the first fluid supply path) with the second fluid (which may originate from the second fluid supply path) to supply the mixed fluid composition towards the sample separation unit for separation of the sample comprised in the fluid composition, and a leak detection unit (or a leak detection system) adapted for detecting (particularly for determining a position of) a leak (for instance a damaged section of a fluid conduit or supply path at which a part of the fluid unintentionally leaves the fluid supply path) upstream (for instance in relation to a fluid flow direction) of or at the mixing point.

According to another exemplary embodiment, a method of leak detection in a system is provided wherein the first fluid is mixed with the second fluid at a mixing point to a fluid composition, and the fluid composition is then supplied for separating a sample introduced (e.g. injected) into the flow of the fluid composition, the method comprising analyzing a volumetric displacement of the first fluid pumped at a predefined pressure, analyzing a fluid flow (e.g. by measuring) at or upstream of the mixing point, and deriving an indication of a leak upstream of or at the mixing point from the analyzed volumetric displacement of the first fluid in conjunction with the analyzed fluid flow at or upstream of the mixing point.

In sample separation systems such as liquid chromatography systems, a sample may be brought in interaction with a sample separation unit, for instance may be trapped on a chromatographic column. A principle of separating different fractions of the sample may then be based for instance on selectively releasing different fractions of the sample from the chromatographic column by conducting a fluidic composition through the column which comprises multiple components. By varying individual contributions of such constituents of such a mobile phase (for instance by applying a so-called gradient), the different fractions may be forced to be released from separation material of the chromatographic column one after the other. A fluid leak in such a fluidic system may have an influence on the performance of a corresponding sample separation experiment. However, it has been considered by the present inventors that a leak at a position upstream of the mixing point, at which mixing point the different components of the mobile phase are mixed with one another, may have a particularly pronounced influence on the separation of a sample since this does not only alter the total volumetric flow rate of a mobile phase passing a sample separation unit but may also influence relative concentrations of constituents of the mobile phase. Such altered composition of the mobile phase may influence the sample components elution in a sensitive manner. Hence, according to an embodiment, particularly the position of a possible leak upstream of a mixing point may be estimated. Corresponding information regarding the leak may then serve as a basis to take necessary measures to prevent undesired impacts of such a leak. For instance, it may be possible to modify, if necessary, the operation mode of the sample separation system to compensate for effects of the leakage. Other appropriate consequences are possible after having located a leak position and its magnitude.

For instance, a leakage in a liquid chromatography system may influence the concentration or mixing ratio of various components of a solvent and may therefore bias the actual composition as compared to target composition. Such a leak can change the retention time of the sample components and/or other critical parameters of the fluidic system. For instance, 1% decrease in the total flow (for instance due to a leak downstream of a mixing point of mixing two or more fluidic components) may shift the retention time by 1% or the like, but 1% change in composition (for instance due to a leak upstream of a mixing point of mixing two or more fluidic components), especially when eluting complex samples with high molecular weight sample components, may even shift the retention time by 200% or the like.

In the following, further exemplary embodiments of the sample separation device and method shall be explained.

The sample separation device may comprise a first displacement pump coupled to the first fluid supply path and configured for pumping the first fluid by a volumetric displacement of the first fluid. The leak detection unit may be configured for detecting or locating the leak by analyzing a displacement of the displacement pump in conjunction with a flow at or upstream of the mixing point when the displacement pump is delivering at a predefined pressure. Such a displacement pump may be a pump having a reciprocating plunger for displacing a fluid volume to thereby pump this fluid volume through the fluidic system. A corresponding displacement may be compared to a flow of the fluid through the fluidic system. Interpreting these two parameters in combination may allow determining a possible leak in the fluidic system.

For instance, the displacement may be preknown (for instance may be known for a specific operation mode of the sample separation system), measured, (for instance detected by a displacement sensor sensing displacement at a position of the displacement pump) or predefined (for instance may be adjusted by adjusting a specific operation mode of the sample separation system).

In an embodiment, the sensor may be a flow sensor, pressure sensor, etc. The flow may be measured directly. It is also possible that the flow is derived indirectly for instance by inspecting a pump behavior.

The leak detection unit may be configured for deriving the flow by monitoring the displacement behavior of the displacement pump over time. For instance, a variation of the displacement behavior (such as a displacement rate) may be analyzed.

The leak detection unit may be configured for detecting or locating the leak by analyzing the displacement of the displacement pump when the flow at or upstream of the mixing point is kept to zero. Maintaining or forcing the flow at zero value may be accomplished by blocking a fluid path, for example by closing a valve.

In addition to the first displacement pump, the sample separation device may comprise a second pump (which may be as well a displacement pump, or may be of any other appropriate pump type) for fluid delivery from a second fluid supply path to the system. The leak detection unit may be configured for detecting or locating the leak by determining whether the flow at or upstream of the mixing point is different from zero. If the flow differs (or differs more than a predefined threshold value) from zero, this may be considered as a decision criteria for assuming the presence of a leak.

In an embodiment, a piston pump may be operated in a constant pressure mode against a fluidically blocked system. The piston drive would first generate pressure in the closed system section by a piston displacement movement until the target pressure is reached, and should then stand still without any pressure decrease, given the fluidically blocked system is leak-free. In case of the occurrence of a leak, the pressure could only be maintained at the desired level by further displacement movement of the piston. Such an event may be interpreted as a leak.

The leak detection unit may be arranged at a position to detect or locate a leak in at least one of the first fluid supply path and the second fluid supply path (or optionally in at least one further fluid supply path upstream a mixing point). Each of the two (or more) fluid supply paths through which the various components of the fluidic composition are conducted (for instance water and an organic solvent such as ACN) individually is considered as a location in a fluidic path at which a leak has a particularly strong disturbing influence on a sample separation experiment. Thus, detecting a leak in these fluid supply paths and locating the leak can increase the reliability of sample separation significantly.

In an embodiment, the leak detection unit may be adapted for performing a fluid supply path specific detection of a leak. Thus, the leak detection unit may be configured in such a manner that a specific fluid supply path may be identified in which the leak has occurred. Therefore, not only the occurrence of a leak may be detected, but it may be found out which of multiple fluidic conduits is the origin of a leak, or to what extent each of the individual channels contributes to the total leak. This may simplify it for an operator to perform a repair and may further serve as a basis for evaluating a qualitative or even quantitative impact of such a leak on a separation procedure. Thus, such channel specific leak detection may allow specifically determining a leak and/or applying an appropriate countermeasure.

Alternatively, in the event that absolute flow sensor readings depend on the solvent in use, the pump can be operated in a mode that one channel (primary) drives the flow, and the respective other channels (secondary) are driven to maintain their flows at zero. This way the absolute scaling (a gain factor may depend on solvent) of the sensor can be neglected. This mode can be cycled across the channels, allowing detecting leak rates for all the channels.

At least a leak-sensitive portion of the leak detection unit may be located at (for instance directly at, adjacent to or close-by) a wearing part of the sample separation device which may be a weak part of a fluidic system and therefore a realistic candidate for the occurrence of a leak. In other words, there may be a close spatial relationship between the leak detection unit and such a wearing part. A wearing part may be considered as a member of a sample separation device which is particularly prone to failure after a certain lifetime which is smaller, particularly significantly smaller, than a lifetime of the sample separation device. Examples for such wearing parts are piston seals or a fluidic valve of a fluidic apparatus. Such wearing parts may have to be substituted from time to time in the sample separation device. When their lifetime is about to end, they may start to become leaky. Such an event can be located according to an exemplary embodiment, and corresponding measures can be taken to substitute these parts in due time.

The leak detection unit may be adapted for quantifying a leak rate (for instance in terms of lost fluid volume or fluid mass per time unit, for example microliters per minute) of a detected and located leak. Thus, the leak detection unit may not only indicate a spatial position or a fluidic conduit or specific part of a sample separation device in or at which the leak is present, but it is also possible that the quantity of the leakage is indicated by the leak detection unit.

In an embodiment, the leak detection unit may be adapted for detecting and locating a leak by executing the following procedure:
  (For instance individually) blocking the first fluid supply path or the second fluid supply path (wherein blocking may mean that the blocked fluid supply path, under the assumption that no leak is present in this fluid supply path, cannot further conduct any liquid since the liquid flow within the corresponding fluid supply path is interrupted at a blocking position);
  Measuring a flow rate dispensed into the blocked fluid supply path in the presence of pressure (in the absence of a leak, blocking may result in a zero flow rate in the blocked fluid supply path; in the presence of a leak, the only way that fluid can be dispensed through the blocked fluid supply path is that the fluid passes the leak, so that the leak rate measured/dispensed in a blocked state is indicative of the extent of the leak); either a reading of a flow sensor or a piston displacement can be used for determining the said flow rate;
  Quantifying a leak rate based on the detected flow rate in the blocked fluid supply path (i.e. a parameter can be determined which includes the information which fluid volume is lost per time unit due to the presence of the leak, wherein the previously measured flow rate can be taken as a basis for this calculation).

Again referring to the previous embodiment, it may be advantageous that the procedure further comprises (for instance between the blocking and the measuring) keeping a provided pressure constant over time in the blocked fluid supply path. Thus, a pump or the like may be functionally coupled with the blocked fluid supply path and may be controlled in such a manner (for instance by providing a pressure sensor reporting a pressure value as a feedback signal to the pump) that the pump provides a constant pressure in this fluid supply path. In such an embodiment, the evaluation of the pump characteristic over time may allow to derive information regarding the flow rate to be measured. Such a procedure of blocking a channel and controlling a pump with a constant pump pressure is a very simple and effective way of quantifying a leak rate.

Alternatives to the above procedure are also possible, one of which will be described in the following. In such an alternative, the leak detection unit may be adapted for detecting and locating a leak by executing the following procedure:
  (For instance individually) blocking the first fluid supply path or the second fluid supply path (wherein blocking may mean that the blocked fluid supply path, under the assumption that no leak is present in this fluid supply path, cannot further conduct any liquid since the liquid flow within the corresponding fluid supply path is interrupted at a blocking position);
  Measuring a pressure decrease in the blocked fluid supply path over time (for instance using a manometer or any other pressure sensor for detecting a characteristic pressure profile over time which may then be indicative of the quantity of a leak, since the pressure in a blocked leak-free fluid supply path should be substantially constant over time);
  Quantifying a leak rate based on the measured pressure decrease over time and based on a preknown capacitance or correlation (for instance stored in a look-up table or provided as a formula correlating leak rate and pressure curve) between leak rate and pressure over time (for instance as a result of a calibration, a correlation between a leak rate and a pressure decrease over time may be determined experimentally, or such a correlation may be derived or calculated theoretically; this information may be used to quantify the leak rate).

The fluid valve is adapted to be switchable between a plurality of operation modes to selectively adjust one of the plurality of operation modes of conducting the first fluid and the second fluid within the sample separation device. Such fluid valve may comprise multiple inlet ports and outlet ports in fluid communication with various fluidic conduits and may be operable automatically or by a user in a way that specific fluidic connections are enabled and others are disabled in accordance with an operation mode of the fluid valve. Disabling specific fluidic paths by the fluid valve may also allow selective blocking or opening of fluidic conduits for locating and quantitatively evaluating leakage rates, for instance indicating where such leakage is present. Since such fluid valves may be provided already in a sample separation device such as a liquid chromatography device, they can be used synergistically for performing a blocking task for leak detection purposes.

The mixing point may be a specific location in a fluidic path at which the two or more fluids are mixed to one another. The mixing point may be a simple junction of fluidic channels or it may be a flow path section, where the flows of the two or more fluids are joined, this point or section being comprised in a mixing unit, mixing device, or mixing appliance further comprising for instance a curved capillary portion at which the different components are promoted to be mixed to one another.

The fluid valve may be adapted for selectively blocking flow of at least one of the first fluid through the first fluid supply path and the second fluid through the second fluid supply path. In a blocked state, any appropriate procedure for quantifying a leak based flow rate may be performed.

In an embodiment, the sample separation device may comprise a trigger unit adapted for triggering a predetermined action in accordance with a leak detection result of the leak detection unit. In case that the leak detection unit has detected and located a leak, this event may be reported by the leak detection unit to a trigger unit which may then be adapted for evaluating this information and, if desired or required, for triggering a specific action. An action being appropriate may depend on the characteristic (for instance the intensity) of the leak which may be decided in accordance with one or more predefined criteria.

For example, the action may comprise triggering an alarm signal or message to provide information to an operator of the sample separation device regarding the detected and located leak. By such an alarm, a user may be informed regarding the leak so that a user may then take the corresponding measures.

In another embodiment, the action triggered by the trigger unit may comprise triggering an alarm providing information to an operator of the sample separation device regarding a replacement part of the sample separation device to be replaced for repairing the leak. By taking such a measure, the system may assist an operator in repairing the system by providing specific hints, information or recommendations on the corrective measures to be taken. Thus, the action may comprise triggering an alarm providing information to an operator of the sample separation device regarding a replacement part of the sample separation device to be replaced for repairing the leak and/or regarding a repair action to be performed.

In still another exemplary embodiment, the action triggered by the trigger unit may comprise triggering an ordering process of a replacement part of the sample separation device to be replaced for repairing the leak.

In another exemplary embodiment, the action triggered by the trigger unit may comprise triggering a modified operation mode (modified as compared to a present operation mode) of operating the sample separation device to at least partially compensate for an influence of the detected and located leak on a performance of the sample separation device. An example for such an embodiment is a liquid chromatography apparatus in which a leak occurs in a fluidic conduit providing one fluid for a multi-component solvent for a gradient run. The present inventors have considered that in such a scenario even a very small leak can cause significant changes of the retention time of analytes and may therefore influence the results of the separation procedure significantly. In order to compensate for such measurement artifacts cause by leakages in the system, the trigger unit may use the derived information regarding the leak to readjust the operation mode of the liquid chromatography device in such a manner that this deterioration of the system properties is compensated. For example, the leaky fluidic conduit may be supplied with a larger amount of liquid than needed for a regular operation which then, after loss due to the leak, results in a proper eluent composition and flow rate according to that as programmed or as would be obtained in a leak-free system.

For instance, the action triggered by the trigger unit may for example comprise a flow rate (for instance a fluid volume or mass delivered per time) of the first fluid and/or of the second fluid being modified (for instance increased).

Other operation modes which can at least partially compensate the influence of a detected leak may also be altered by the system upon detection of the leak. In all these cases, it is possible that a user is additionally informed about the machine triggered modification of the operation mode.

In an embodiment, the action triggered by the trigger unit may comprise a modified operation mode of operating the sample separation device so as to perform a defined target operation mode of the sample separation device adjusted by an operator prior to the occurrence of the leak. Therefore, when a leak has occurred and the previously adjusted by the operator parameters do not match anymore in view of the impact of the leak, the system may automatically suggest or perform a manipulation of the operation parameters which can compensate the effect of the leak partially or completely. For example, the action may comprise operating a pump delivering a respective fluid to a respective fluid supply path having a detected and located leak with an increased flow rate as compared to a leak-free operation in accordance with a leak rate in the respective fluid supply path.

In some scenarios a leak may occur at a defective or damaged sealing. In these and other cases, knowledge of the position of the leak in an individual channel may be used for compensating corresponding artifacts so that a target result may still be achieved. However, taking this measure may require the knowledge of the leak position in a channel specific manner. Upon detection and location of such a leak on a channel-based level, a pre-warning function may be implemented indicating a user that a sealing or any other wearing part leaks and should be replaced. In such a case, the device itself may trigger ordering a new seal and may operate, until the new seal is delivered, with a specific compensation. In an embodiment, when a leak is detected, a compensation mode may be activated so that the device delivers analysis results like a properly operating device would do, due to the specific leak compensation.

The sample separation device may be adapted as a fluid separation system for separating components of the sample. When a mobile phase including a fluidic sample passes through the fluidic device, for instance driven by high pressure, the interaction between the column packing and the fluidic sample may allow for separating different components of the sample, as performed in a liquid chromatography device.

The sample separation device may also be adapted as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the column packing the different samples may be distinguished, and one sample or band of material may be selectively isolated as a purified sample.

The sample separation device may be adapted to analyze at least one physical, chemical and/or biological parameter of at least one component of the mobile phase.

Embodiments of the present invention might be embodied based on most conventionally available HPLC systems, such as the Agilent 1290 Series Infinity system, Agilent 1200 Series Rapid Resolution LC system, or the Agilent 1100

HPLC series (all provided by the applicant Agilent Technologies—see www.agilent.com—which shall be incorporated herein by reference).

The sample fluid might comprise any type of process liquid, natural sample like juice, body fluids like plasma or it may be the result of a reaction like from a fermentation broth. It may also comprise (but not limited to) sea water, mineral oil or any rectification or cracking fractions of it, extracts of soil, plants or artificial materials such as plastics, as well as alcoholic or alcohol-free beverages.

The pressure in the mobile phase might range from 2-200 MPa (20 to 2000 bar), in particular 10-150 MPa (100 to 1500 bar), and more particular 50-120 MPa (500 to 1200 bar).

The HPLC system might further comprise a sampling unit for introducing the sample fluid into the mobile phase stream, a detector for detecting separated compounds of the sample fluid, a fractionating unit for collection of separated compounds of the sample fluid, or any combination thereof.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

FIGS. 2A-2E illustrate an embodiment of the fluidic valve 116 as a 7-port valve.

DETAILED DESCRIPTION

Figure 1A:
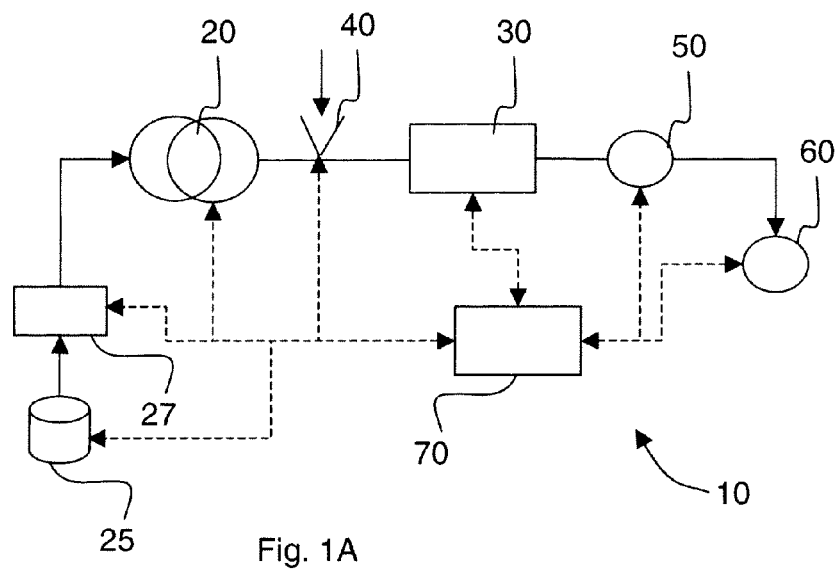
FIG. 1A shows a liquid separation system 10, in accordance with embodiments of the present invention, e.g. used in high performance liquid chromatography (HPLC).

Referring now in greater detail to the drawings, FIG. 1A depicts a general schematic of a liquid separation system 10. A pump 20 receives a mobile phase from a solvent supply 25, typically via a degasser 27 which reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as introduce or inject) a sample fluid into the mobile phase. The stationary phase of the separating device 30 is adapted for separating compounds contained in the sample. A detector 50 can be provided for detecting separated compounds of the sample. A fractionating unit 60 can be provided for collection of separated compounds of the sample.

While the mobile phase can be comprised of one solvent only, it may also be mixed from plurality of solvents. Such mixing might be a low pressure mixing and provided upstream of the pump 20, so that the pump 20 already receives and pumps the mixed solvents as the mobile phase. Alternatively, the pump 20 might comprise plural individual pumping units, each of those receiving and delivering a different solvent or mixture, so that the mixing of the mobile phase (as delivered to the separating device 30) occurs at high pressure and downstream of the pump 20 (or within thereof). The composition of the mobile phase may be kept constant over time, the so called isocratic mode, or varied over time in a controlled manner, the so called gradient mode.

A control and data processing unit 70, which can be a conventional PC, workstation or a dedicated controller, might be coupled (as indicated by the dotted arrows) to one or more of the devices in the liquid separation system 10 in order to receive information and/or to control the operation. For example, the control and data processing unit 70 might control operation of the pump 20 (e.g. setting control parameters) and receive therefrom information regarding the actual working conditions (such as output pressure, flow rate, etc. as measured within the separation system 10 or at certain locations in the flow path, e.g. within the pump unit 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as pressure over time, flow rate, vacuum level, etc.). The data processing unit 70 might further control operation of the sampling unit 40 (e.g. controlling sample injection). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50).

Figure 1B:
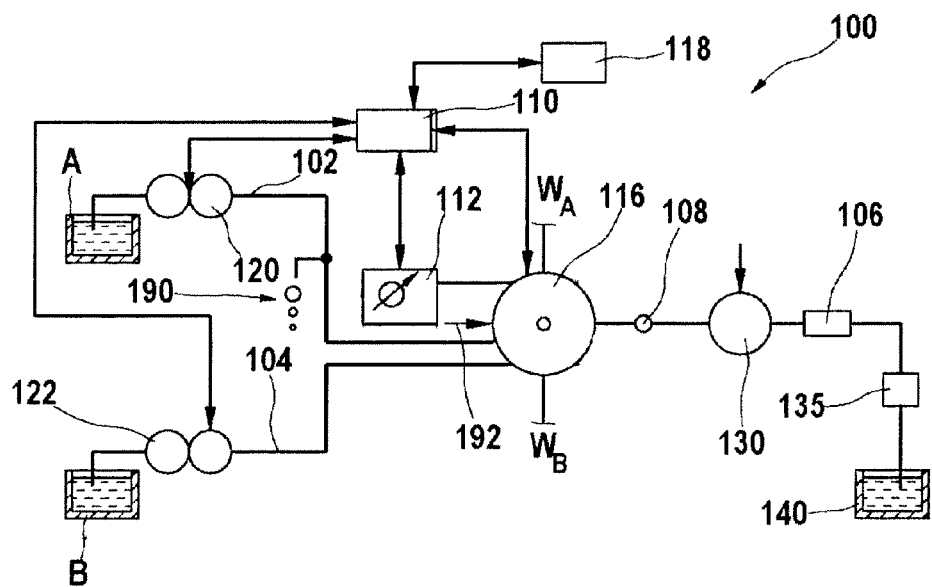
FIG. 1B illustrates a liquid chromatography system according to an exemplary embodiment.

FIG. 1B depicts a liquid separation system 100 according to an exemplary embodiment. Pumps 120, 122 (corresponding together to the pump 20 of FIG. 1A) drive a mobile phase through a separating device 106 (which corresponds to the separating device 30 in FIG. 1A, and might be a chromatographic column). A sampling unit 130 (corresponding to the sampling unit 40 in FIG. 1A) can be provided in a fluidic path between the pumps 120, 122 on the one hand and the separating device 106 on the other hand in order to introduce a sample fluid into the mobile phase. The separating device 106 (e.g. a chromatographic column) is adapted for separating compounds of the sample liquid. A detector 135 (which corresponds to the detector 50 in FIG. 1A, and might for instance be a UV detector) may detect different fractions of the fluidic sample separated in the separating device 106. A fractionating unit 140 (corresponding to the fractionating unit 60 in FIG. 1A), or alternatively a waste reservoir, can be provided for collection of separated compounds of the sample.

The liquid chromatography device 100 is adapted for separating a sample injected at the sample injection unit 130 using a mobile phase comprising a first fluid A (indicated by a reservoir) and a second fluid B (also indicated by a reservoir). A first fluid conduit 102 is provided for conducting the first fluid A. A second fluid conduit 104 is provided for conducting the second fluid B. The first fluid may be water and the second fluid may be an organic solvent such as acetonitrile, ACN. Water is provided from a water vessel denoted with A, and ACN is provided from an organic solvent vessel denoted with B. The pump 120 together with the first conduit 102 provides a first supply channel (denoted for the sake of simplicity as supply channel A) for supplying the first fluid A towards the separating device 106. Accordingly, the pump 122 together with the second conduit 104 provides a second supply channel (denoted for the sake of simplicity as supply channel B) for supplying the second fluid B towards the separating device 106.

The first fluid conduit 102 and the second fluid conduit 104 are coupled to a fluidic valve 116, which further couples to a first waste output $W_A$, a second waste output $W_B$, a system output denoted as 108, and a sensor 112. In this embodiment, the sampling unit 130 and the separating device 106 shall represent a pressure system experiencing high pressure in operation, which pressure system is then located upstream to the system output 108 and coupling thereto. A possible leak 190 is symbolically shown as originating from a separate fluid conduit. In practice a leak can occur anywhere within the system and is not linked to any specific capillary conduit or part in the flow path.

FIGS. 2A-2E illustrate an embodiment of the fluidic valve 116 as a 7-port valve having 5 different switching positions. The fluidic valve 116 has 6 outer ports (denoted 1, 4-8) and one center port (denoted by S). Port 1 is externally connected to the second waste output $W_B$, port 4 is externally connected to the first waste output $W_A$, port 5 is externally connected to the first fluid conduit 102 (also denoted by A indicating the first supply channel A providing the first fluid A). The sensor 112 is externally connected between the ports 6 and 7. Port 8 is externally connected to the second fluid conduit 104 (also denoted by B indicating the second channel B providing the second fluid B). The center port S may represent or is externally connected to the system output 108.

The fluidic valve 116 further has three grooves 150, 152 and 154, each being configured to couple between two ports, i.e. to provide a fluidic connection between the two ports. While the grooves 150, 152 and 154 in FIG. 2 are depicted to couple between adjacent ports, it is well known in the art that such grooves can be provided for coupling between any of the ports.

The fluidic valve 116 further has a fourth groove 155, which couples between the center port S and the groove 152, thus coupling the center port S with an outer port or several outer ports, typically two outer ports.

FIG. 2A depicts a first switching state of the fluidic valve 116. The first conduit 102 and the second conduit 104 are coupled via the groove 150, the sensor 112, and the grooves 152 and 155 to the system output 108 at port S. In this state, the first conduit 102 provides the first fluid A, and the second conduit 104 provides the second fluid B, which fluids A and B are then mixed (starting at a mixing point 156 provided be the connection of the grooves 152 and 155), and supplied to the pressure system via port S. The second waste output $W_B$ is blocked via groove 154. Accordingly, the first waste output $W_A$ is also closed, as no groove is coupling to port 4 in this state. This is a "normal operation position" of the valve.

FIG. 2B depicts a second switching state of the fluidic valve 116, which corresponds in function with the first switching state shown in FIG. 2A. Again, the first conduit 102 and the second conduit 104 are coupled to the system outlet S, here via the groove 154, the sensor 112, and the grooves 152 and 155. Accordingly, the first conduit 102 provides the first fluid A, and the second conduit 104 provides the second fluid B, which fluids A and B are then mixed (starting at the mixing point 156 provided be the connection of the grooves 152 and 155), and supplied to the system via port S. The first waste output $W_A$ is blocked via groove 150. The second waste output $W_B$ is also closed, as no groove is coupling to port 1 in this state. This is another "normal operation position" of the valve.

FIG. 2C depicts a third switching state of the fluidic valve 116. The first conduit 102 (coupled to port 5) is coupled via the groove 150 to the first waste output $W_A$. The second conduit 104 (coupled to port 8) is coupled via the groove 154 to the second waste output $W_B$. The system (at outlet S) is coupled via the grooves 152 and 155 to the sensor 112. In this state of the valve 116, both supply channels A and B can be purged (individually).

FIG. 2D depicts a fourth switching state of the fluidic valve 116. The first conduit 102 is coupled via the groove 154 to the sensor 112, which is blocked at one end (port 7). The system output 108 (see FIG. 1B) is connected via the grooves 152 and 155 to the first waste output $W_A$. The second waste output $W_B$ is blocked via groove 150. In this state, the first supply channel A is connected to the sensor 112, thus allowing to measure a flow property (e.g. flow rate, pressure, etc.) in the first supply channel A during the end of the related flow path is blocked, which might e.g. facilitate determining of a leakage in the first supply channel A, as will be explained in more detail later.

FIG. 2E depicts a fifth switching state of the fluidic valve 116. The second conduit 104 is coupled via the groove 150 to the sensor 112, which again is blocked at the other end (port 6). The system output 108 is connected via the grooves 152 and 155 to the second waste output $W_B$. The first waste output $W_A$ is blocked via groove 154. In this state, the second supply channel B is connected to the sensor 112, thus allowing to measure a flow property (e.g. flow rate, pressure) in the second supply channel B during the end of the related flow path is blocked, which might e.g. facilitate determining of a leakage in the second supply channel B, as will be explained in more detail later.

The first and second switching states (as depicted in FIGS. 2A and 2B) represent "normal supply" operation for supplying the pressure system (at the system output 108) with a mixture of the fluids A and B as provided by the supply channels A and B. The sensor 112 measures a flow property (e.g. flow rate, pressure) substantially at (or close before) the mixing point 156, so that the measured property may be regarded as being representative for the output flow into the pressure system at port S. E.g. in case the sensor 112 measures pressure, the measured pressure represents a system pressure at port S. The first and second switching states are substantially equivalent and exchangeable in function, so that operating in only one of both states can be sufficient for most applications.

The third switching state (FIG. 2C) represents a purging state allowing to purge one or both of the supply channels A and B directly to waste. An additional advantage is that the channels open to waste via independent conduits, thus avoiding the possibility that a pressure drop generated by one channel could prevent another channel from being properly purged. The fourth and fifth switching states (FIGS. 2D and 2E) represent diagnosis states, each for diagnosing one of the first and second channels A and B, e.g. with respect to leakage. In all three of the third, fourth and fifth state, the system S is disconnected from fluid supply of either one or both of the supply channels A and B.

The configuration of the valve 116 thus allows using one sensor 112 for sensing during "normal supply" a flow property representative for the output flow into the system S, as well as for diagnosing each one of the first and second channels A and B separately. In other words, by using this configuration only one sensor 112 is sufficient for all three measuring tasks.

In the following the effect of leakage shall be illustrated. In the scenario shown in FIG. 1B, a leak has occurred at a position 190 within the first fluid conduit 102. The leak 190, which might e.g. be a connection point between the pump 120 and the first fluid conduit 102, shall be represented here for the sake of simplicity as an extra leak conduit 190. Hence, the solvent A leaks and is partially lost before reaching the mixing point 156 (at the crossing of grooves 152 and 155 in the valve 116). Consequently, the total volumetric flow is lower than expected, and the compositional ratio between the A, e.g. water and B, e.g. ACN at a position downstream the mixing point 156 does not follow any longer the desired and preset composition ratio of flows between water and ACN, whereas the ratio of the both flows A and B might have been still correct at a position in the fluid conduits 102 and 104 upstream the leak 190.

The mixing point 156 is in fluid connection with and arranged downstream of (in a fluid flow direction indicated with an arrow 192 in FIG. 1) the first fluid conduit 102 and the second fluid conduit 104, and is adapted for mixing the first fluid A from the first fluid conduit 102 with the second fluid B from the second fluid conduit 104 to supply the mixed fluid composition (A+B) towards the separation column 106 for separation of the sample. As the retention time of sample components (analytes) is strongly dependent on the composition of the mobile phase, the retention times and consequently identification and quantification of the analytes may be affected.

As will be described in the following in more detail, leak detection in the liquid chromatography system 100 is provided for detection, quantitative determination or even spatial locating the position 190 of the leak upstream of the mixing point 156. In the present scenario, leak 190 has occurred in the first fluid conduit 102. Correspondingly, the liquid chromatography system 100 is also capable of locating such a leak in the second fluid conduit 104.

In the embodiment of this scenario, the sensor 112 is adapted for determining a system parameter, as e.g. pressure. The sensor signal or reading is reported to a control unit 110 (which corresponds to the data processing unit 70 in FIG. 1A). The control unit 110 may have processing capabilities and may, for instance, be configured as a microprocessor or a central processing unit (CPU). Apart from the data communication with the sensor 112, the leak detection unit 110 may also be in data communication with the pumps 120, 122 and with the fluidic valve 116. The leak detection unit 110 may centrally control operation of the liquid chromatography device 100. Based on the sensor reading and control or feedback signals from the pump 102, the internal calculating facilities of the pump and/or the leak detection unit 110 can evaluate the volume loss or leak in the fluid conduits.

A channel-specific detection of the leak may be performed based on fluid displacement rates and sensor 112 output signals when operating the valve 116 in either one or both diagnosis states as depicted in FIGS. 2D and 2E. For example, in the present scenario, the leak 190 occurs in the first fluid channel 102. This leak can be detected as follows:

The leak detection unit 110 may be adapted to control pumps 120, 122 coupled to the first fluid conduit 102 and in the second fluid conduit 104 in such a manner that a fluid is delivered through only one of the first and the second fluid conduit 102, 104 whereas the system condition as pressure is monitored by the sensor 112 while the valve 116 is in its corresponding diagnostic position. The other fluid channel is preferably switched off or the flow generation is disabled. More specifically, the control unit 110 may control the pumps 120 and 122 in such a manner that the fluid is displaced through one of the fluid conduits 102, 104 such that a desired pressure on the sensor is generated, while no fluid is meant to be transported out the fluidic conduit 102, 104 towards the mixing point 156 due to the blockage of the coupled conduit after the sensor 112 by the switching valve in its corresponding diagnostic position.

In this blocked state (corresponding to the diagnosis state according to FIG. 2D), the control unit 110 may trigger the pump 120 to operate in such a manner, that 112 signal or readings of the pressure sensor are preferably maintained constant after they have achieved a desired value The flow rate necessary for maintaining the constant value of the sensor signal may be evaluated by the control unit 110, based on the commanded displacement speed or measured drive or piston movement of the pump 120, for quantifying a leak rate of the blocked first fluid conduit 102. During such a procedure, the pump 120 is preferably controlled to keep the pressure in the blocked first fluid conduit 102 constant over time. Therefore, the entire flow rate in the first fluid conduit 102 in the blocked state with the pump 120 operating with a constant pressure results from the leak 190, which can therefore be quantified, for instance by reading the commanded speed of the pump 120.

Upon detection of such a leak, the control unit 110 may report the corresponding event to a trigger unit 118. The trigger unit 118 may be adapted for triggering an appropriate action in accordance with a location result of the detected leak, and/or in accordance with the quantity of the leakage. For example, the trigger unit 118 may trigger an alarm indicating to a user that a leak has occurred and that this leak has occurred in the first fluidic channel 102. The trigger unit 118 may also indicate to the user a probable origin of the leak 190.

Furthermore, the trigger unit 118 may trigger a modified operation mode of operating the liquid chromatography device 100 to compensate for an influence of the detected and located leak on a performance of the sample separation device 100. For this purpose, the control unit 110 may evaluate which influence the position and/or the quantity of the leak 190 has on a sample separation procedure of the liquid chromatography device 100. The control unit 110 may then control the pump 120 in such a manner that fluid A is provided in excess so that, under consideration of the leakage loss at the leak 190, a correct amount of fluid A is delivered at the mixing point 156, so that the chromatographic experiment can be run as with a liquid chromatography apparatus 100 being substantially leak-free.

In the following, some basic considerations of the present inventions will be described, based on which exemplary embodiments have been developed.

In an embodiment, the detection, calibration and correction of leaks in individual channels of gradient pumps may be performed.

In liquid chromatography (LC) reproducibility of the following value is an important performance parameter of a corresponding separation device:

Retention time (Rt): a run time at which a peak of a given analyte is detected.

Peak area (PA): integrated detector signal from peak begin to end for a given analyte (for instance integrated UV-detector signal over time as [mAU·s]).

In HPLC (High Performance Liquid Chromatography) separations, reproducibility of retention times and in certain applications also the peak areas in the sub-digit percent range is expected. This leads to the requirement that all influential factors should be controlled to an optimum precision. In Reverse-Phase Liquid Chromatography, large molecules (like for instance proteins) may exhibit a steep adsorption isotherm, which generally means that minute changes in eluent composition may influence the retention time dramatically.

For a given analyte, retention time is generally dependent on column type and geometry, its temperature, the actual flow rate and the actual mobile phase composition. While the column type and geometry may be pretty stable parameters, temperature, flow rate and solvent composition may easily show variance. This holds for pumping systems which generate solvent flow and composition by delivering individual flows of for instance water and organic solvent to the system. During sample separation operation the separation column is held in a controlled environment, like a column oven. So, temperature variations may be suppressed to a sufficient extent.

On the side of total flow rate through the system, its influence on the retention times may be considered to be almost a 1/x relation, which results in about 1% shift in retention time for a 1% lower flow rate. If the retention time is expected in a 1% window with a total flow of 500 μl/min, a leak rate below 5 μl/min may still be acceptable.

However if the leak occurs at a point in the system which is upstream from the mixing point, then there is an additional impact also on solvent composition. At an expected composition of for instance 15% B and total flow of 500 μl/min, the same 5 μl/min leak in the organic (B) channel may shift the solvent composition to almost 14% B. But in case of steep adsorption isotherm this may result easily in a 50% increase of the retention time. Thus blending the precise solvent composition may requirement a 50 times higher precision as compared to requirements on flow rate, to achieve the same retention time precision. In view of these considerations, it is vital not only to know about the fact of existence of a leakage, but also to know its magnitude and where (in which part solvent path or pump channel) the fluid loss occurs.

On the basis of these considerations, particularly the following embodiments have been developed.

For precise pumping actions, both in total flow rate and in solvent composition, either a leak free condition is needed or the leak needs to be corrected for. While in most cases a leak behind (i.e. downstream of) a mixing tee (T) may be tolerated, even minor leaks in the individual pumping channels may affect the retention times because of the amplification effect if the adsorption isotherm appears to be steep enough.

Severe leaks are detectable as liquid dropping down, while minor leaks (for instance smaller than 5 μl/min) often hide long and may be hard to diagnose, since the liquid (especially organic solvent) evaporates fast enough. Usually, a detected leak is a reason to repair, which then is followed by leak diagnostic (to increase reliability).

Leak correction according to exemplary embodiments is based on the approach to quantify the leak, especially identified in individual channels, followed by setting the control of these channels to correct for the flow loss.

If for a given pressure level the current leak rate is known, a correction may be performed by adding the leak rate onto the commanded flow rate for the affected pump channel.

In the case of gradient elution, there is usually also a viscosity gradient overlaid, which in turn results in a pressure change (under constant flow operation) across the gradient time. In order to perform a decent leak correction in the case of gradients, it may be necessary to know the actual leak rate all across the pressure range (at least the pressure range as experienced during the gradient analysis).

It is possible to qualify individual channels for their leak behavior. First, the channels may have some independent signal to monitor their pressure. Then the channels may have some feature to block them individually upstream of the mixing junction. Leak rate may then be quantified by setting a flow rate, which results in a flat pressure profile (keep pressure) at the pressure level where the leak rate is to be investigated. For instance, this can be done at several steps across the entire pressure range (for instance at pressure values of 200 bar, 400 bar, 600 bar, 800 bar, 1000 bar, 1200 bar).

Stepwise test architectures may be advantageous, because in this case influence of the hydraulic capacitance and the thermal behavior of the liquid may be avoided. Interpreting leak rates under non-constant pressure conditions may require more complex algorithms and an extra set of parameters to achieve reliable measurement results.

In the "keep pressure" approach if a plugged hydraulic system into which a minute amount of flow is delivered, magnitude of which is controlled to achieve a flat constant pressure profile, it may be sufficient to use an averaging function to derive a precise quantitative reading. These readings correlated to the pressure levels at which they were derived represent a matrix of leak rates over the pressure.

Still another (preferable) possibility is reading out the physical piston positions as provided by the control mechanism or by the position feedback circuitry at two or more moments over time, whereas the pressure is kept constant. The piston displacement over the time interval between readings will reflect the liquid volume lost during this time interval, which represents the leak flow rate During operation in leak correction mode, each individual channel may refer to the look-up table of leak rates according to the actual pressure and add this rate to the commanded displacement value. This way, the individual dispensing rates may be increased by exactly the volumetric loss in that channel, which is actually given at real time under real pressure condition. Net result would thus at least be improved, if not precise in terms of flow rate and composition being delivered at a point behind (say downstream) the mixing tee.

System leak rate (downstream from the mixing tee) can also be compensated for, but this has to be calibrated in an extra step and added to the total flow rate correspondingly to the contributions of the individual channel flow rates.

Figures 3, 4:
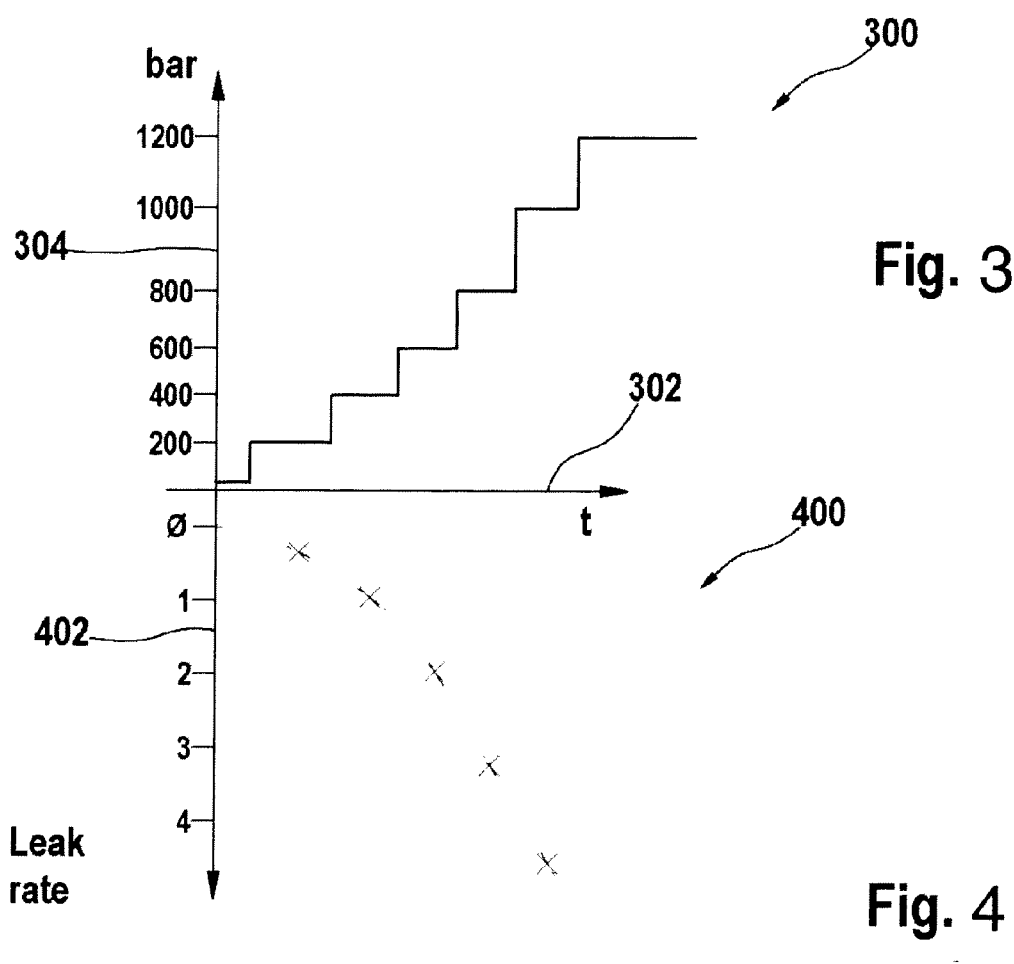
FIG. 3 is a diagram showing a relation between a programmed pressure of a pump in a test and the time.
FIG. 4 is correlated to FIG. 3 and shows a corresponding relation between a leak rate and the time, when the programmed pressure is applied.

FIG. 3 shows a diagram 300, and FIG. 4 shows a diagram 400 sharing a common abscissa 302 along which the time is plotted. Along an ordinate 304 of the diagram 300 and along an ordinate 402 of the diagram 400, the pressure in bar and the corresponding measured leak rate is plotted, respectively. Thus, FIG. 3 and FIG. 4 show an example of correlation between leak rate and pressure of a separation device as can be determined in the diagnostic operation.

FIG. 5 illustrate another embodiment of the fluidic valve 116 as a 7-port valve. The fluidic valve 116 has 6 outer ports (denoted 601-606) and one de-centrally situated system port (denoted by S). Port 601 is externally connected to the second waste output $W_B$, port 602 is externally connected to the first waste output $W_A$, port 603 is externally connected to the first fluid conduit 102 (also denoted by A indicating the first supply channel A providing the first fluid A). The sensor 112 is externally connected between ports 604 and 605. Port 606 is externally connected to the second fluid conduit 122 (also denoted by B indicating the second channel B providing the second fluid B). The center port S is externally connected to the system output 108.

The fluidic valve 116 further has two grooves 610 and 620, each being configured to provide a fluidic connection between two ports. While the grooves 610 and 620 in FIG. 5 are depicted to couple between adjacent ports, it is well known in the art that such grooves can be provided for coupling between any of the ports.

The fluidic valve 116 further has a third groove 625, which in one of the positions can connect the de-central system port S to the groove 620, thus coupling the de-central port S with certain outer ports.

Figure 5A:
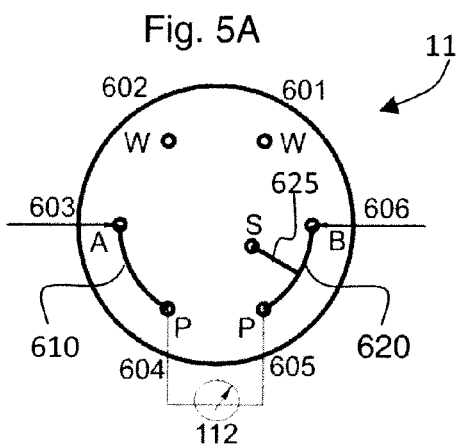
FIGS. 5A-5D illustrate another embodiment of the fluidic valve.

FIG. 5A illustrates a normal operating position of the valve, in which the fluid provided by the supply channel A via conduit 102 passes through the pressure sensor 112 to the mixing point and then via the groove 625 as mixture with the fluid B to the system port S. The fluid provided by the supply channel B via conduit 122 passes to the mixing point and then via the groove 625 as mixture with the fluid A to the system. The pressure sensor measures in this case the system pressure as it is an unconstrained connection to the system port of the pump.

Figure 5B:
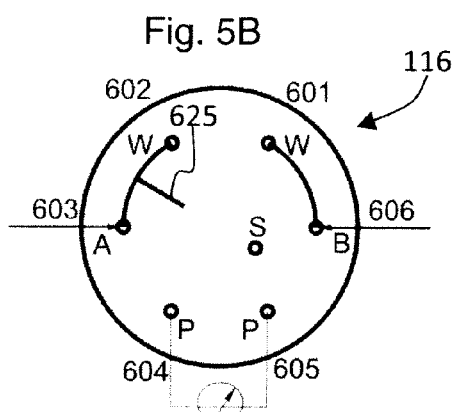

FIG. 5B illustrates the purge position of the valve. The supply channels A and B are connected via the grooves 620 and 610 immediately to the waste ports 602 and 601, thus facilitating immediate purging of the fluids provided by these pumps to the waste.

Figure 5C:
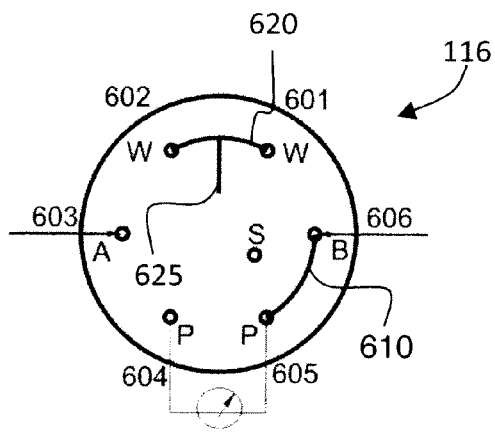

FIG. 5C illustrates a diagnostic position for the supply channel B. In this case the conduit 122 and the groove 610 connect the supply channel B to the pressure sensor 112, the second port 604 of which is blocked by the valve. Thus a diagnostic procedure on the supply channel B is facilitated by connecting this supply channel B to the pressure sensor and blocking the fluid path downstream of it.

Figure 5D:
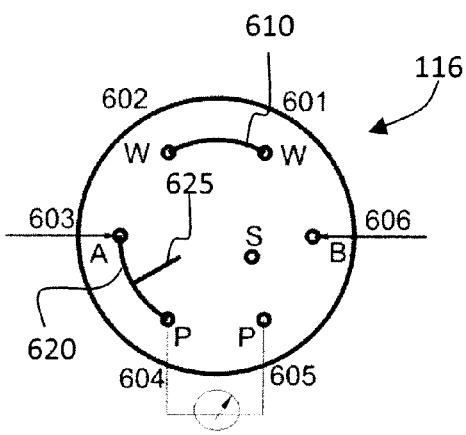

FIG. 5D illustrates a diagnostic position for the supply channel A. In this case the conduit 102 and the groove 620 connect the supply channel A to the pressure sensor 112, the second port 605 of which is blocked by the valve. The groove 625 is also blocked thus not having any influence on the course of the diagnostic procedure. Thus a diagnostic procedure on the supply channel A is facilitated by connecting this supply channel A to the pressure sensor and blocking the fluid path downstream of it It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A sample separation device for separating a sample, the sample separation device comprising:
   a first fluid supply path for supplying a first fluid,
   a second fluid supply path for supplying a second fluid,
   a sample separation unit adapted for separating the sample,
   a sensor configured for determining a value of a parameter related to the fluid, and
   a valve configured for selectively coupling both of the first and second fluid supply paths to the sensor and to the sample separation unit; or coupling one of the first and second fluid supply paths to the sensor, while blocking the fluid supply path with the sensor coupled to the fluid supply path.

2. The sample separation device according to claim 1, wherein the valve is further configured for joining the first and second fluid paths together while coupling both of the first and second fluid supply paths to the sensor and to the sample separation unit.

3. The sample separation device according to claim 1, wherein the valve is further configured for coupling at least one of the first and second fluid supply paths to a waste outlet.

4. The sample separation device according to claim 1, wherein the valve is configured for coupling one of the first and second fluid supply paths to the sensor.

5. The sample separation device according to claim 1, wherein the parameter measured by the sensor is related to a state of the fluid.

6. The sample separation device according to claim 1, wherein the parameter measured by the sensor is one of pressure and flow rate of the fluid.

7. The sample separation device according to claim 1, comprising:
   a mixing point in fluid communication with and arranged downstream of the first fluid supply path and the second fluid supply path and being adapted for joining the first fluid path with the second fluid path to supply a mixed fluid composition towards the sample separation unit for separation of the sample comprised in or introduced into the fluid composition, and
   a leak detection unit adapted for detecting a leak upstream of or at the mixing point.

8. The sample separation device according to claim 7, comprising:
   a first displacement pump coupled to the first fluid supply path and configured for delivery of the first fluid by a volumetric displacement of the first fluid;
   wherein the leak detection unit is configured for detecting the leak by analyzing a displacement generated by the displacement pump in conjunction with a fluid flow at or upstream of the mixing point, when the displacement pump is delivering a fluid at a predefined pressure.

9. The sample separation device according to claim 8, wherein the leak detection unit is configured for deriving the value of an actual fluid flow by monitoring the displacement behavior of the displacement pump over time.

10. The sample separation device according to claim 7, wherein the leak detection unit is configured for detecting the leak by analyzing the displacement generated by the displacement pump, during the flow at or upstream of the mixing point is set or forced to zero.

11. The sample separation device according to claim 7, wherein the sample separation device comprises a second pump for pressurizing the second fluid supply path to the predefined pressure, wherein the leak detection unit is configured for detecting the leak by determining whether the flow at or upstream of the mixing point is different from zero.

12. The sample separation device according to claim 1, wherein the sample separation device is adapted to analyze at least one physical, chemical and/or biological parameter of at least one compound of a sample.

* * * * *